(12) United States Patent
Hibbs, Jr.

(10) Patent No.: US 7,568,797 B2
(45) Date of Patent: Aug. 4, 2009

(54) PROTECTIVE FACIAL SHIELDING HAVING MAGNETIC RIMS

(76) Inventor: Harry O. Hibbs, Jr., 622 1/2 Fayette St., Washington, PA (US) 15301

( * ) Notice: Subject to any disclaimer, the term of this patent is extended or adjusted under 35 U.S.C. 154(b) by 120 days.

(21) Appl. No.: 11/804,820

(22) Filed: May 21, 2007

(65) Prior Publication Data

US 2007/0273822 A1 Nov. 29, 2007

Related U.S. Application Data

(60) Provisional application No. 60/803,052, filed on May 24, 2006.

(51) Int. Cl.
*G02C 1/00* (2006.01)
(52) U.S. Cl. ................ 351/158; 2/431; 2/449

(58) Field of Classification Search .......... 351/41, 351/158; 2/12, 15, 426–454
See application file for complete search history.

(56) References Cited

U.S. PATENT DOCUMENTS 4,547,909 A * 10/1985 Bell .................. 2/431
6,098,207 A * 8/2000 Burtin ................ 2/431

\* cited by examiner

*Primary Examiner*—Huy K Mai
(74) *Attorney, Agent, or Firm*—Buchanan Ingersoll & Rooney PC

(57) ABSTRACT

An improved pair of safety glasses is provided with magnets to prevent flying debris, such as metal shavings, striking the face and endangering the eyes. Magnetic strips are disposed around the periphery of the safety glasses or embedded in grooves defined around the edge of the glasses. The magnetic strips will tend to attract any flying metal debris which may strike the safety glasses near the edges thereof, preventing metal particles from infringing the facial area, and, in particular, the area surrounding the eyes.

12 Claims, 1 Drawing Sheet

PROTECTIVE FACIAL SHIELDING HAVING MAGNETIC RIMS

CROSS-REFERENCE TO RELATED APPLICATIONS

This application claims the benefit of co-pending provisional patent application Ser. No. 60/803,052 entitled "Protective Facial Shielding Having Magnetic Rims", filed on May 24, 2006, the entire disclosure of which is incorporated by reference herein.

FIELD OF THE INVENTION

The present invention relates to the field of safety glasses and more particularly to improved safety glasses having the ability to prevent small airborne metallic objects from lodging in the wearer's eyes.

BACKGROUND OF THE PRIOR ART

Safety glasses and other protective face shields have been used to cover the wearer's eyes and shield objects from and protect the wearer from airborne debris. For the most part, the safety glasses tend to work fine for larger sized debris. However, smaller sized debris may float around the spacing between the wearer's face and the safety glasses. Oftentimes, such debris becomes lodged in the wearer's eyes. This is especially dangerous when the debris is metallic in nature and can cause serious damage to the eyes. There is a need for improved safety glasses which provide further protection against airborne metallic debris.

SUMMARY OF THE INVENTION

The invention is an improvement to existing safety glasses and other protective eyewear, such as full face shields. Such protective wear is normally worn in situations where there is a danger of flying debris, such as metal shavings, striking the face and endangering the eyes. The invention is particularly useful for anyone using a metal grinding apparatus which may generate flying metal shavings or debris, such as persons employed in auto body shops, brake shops, machine shops and the like.

The improved protective wear, according to the invention, will have magnetic strips disposed around the periphery of the device, as shown in the accompanying figure. Shields and eyeglasses of this type are typically manufactured of polycarbonate or other hard transparent material. The magnetic strips may be embedded in grooves defined around the edge of the device, clipped on, glued on, attached in some manner to the frames of the eyeglasses, or attached in any other way commonly known in the art. Additionally, the magnetic strips may be rounded such that they form the frames or outer edges of the polycarbonate area.

The magnetic strips will tend to attract any flying metal debris which may strike the device near the edges thereof, preventing metal particles from infringing the facial area, and, in particular, the area surrounding the eyes.

DETAILED DESCRIPTION OF THE PREFERRED EMBODIMENTS

Figure 1:
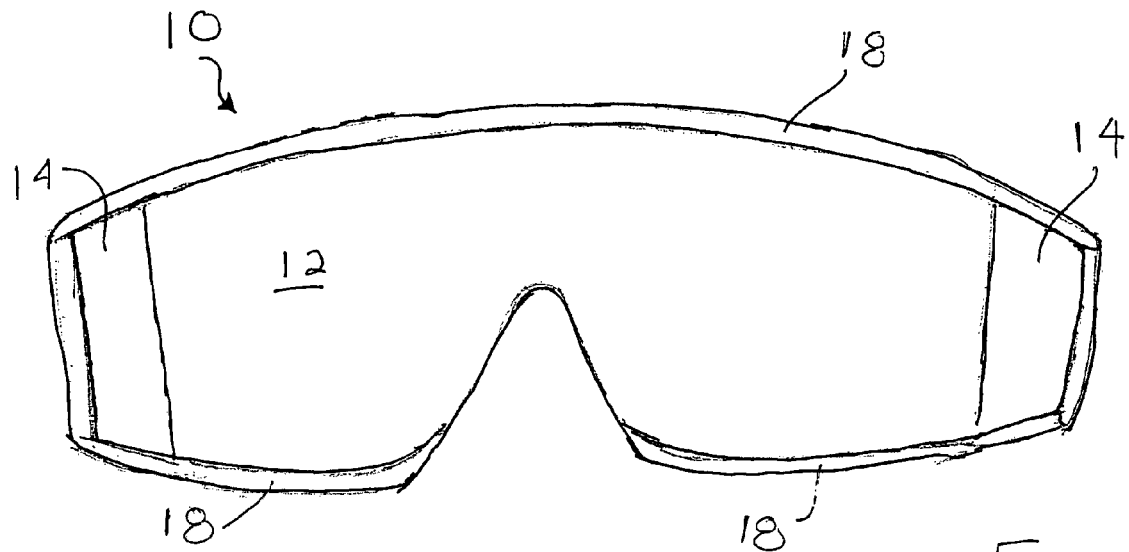
FIG. 1 is a front view of a preferred embodiment of the safety glasses of the present invention.
Figure 2:
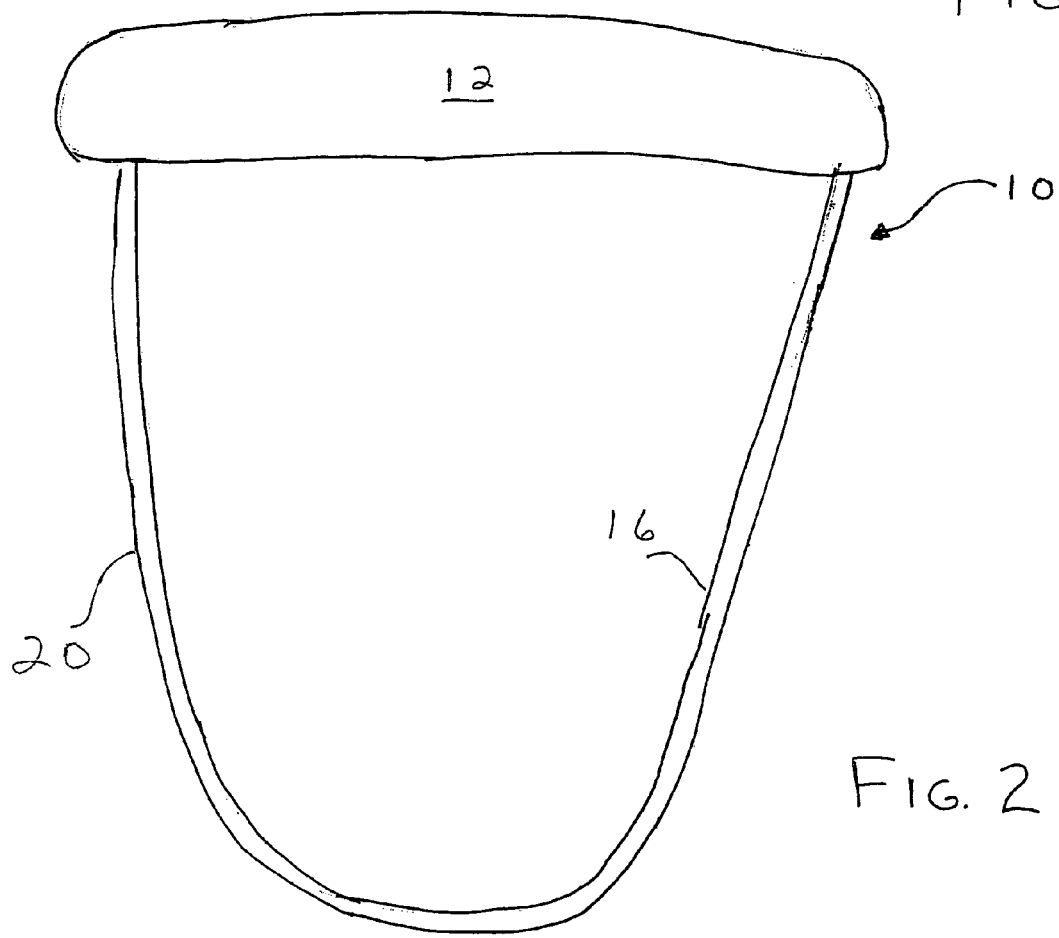
FIG. 2 is a top view of the safety glasses of FIG. 1.

As shown in FIGS. 1 and 2, safety glasses 10 include face shield 12, side shield 14 and fastening strap 16. Alternatively, safety glasses 10 could replace fastening strap 16 with a pair of temples or other device that would generally secure safety glasses 10 to the wearer. In the preferred embodiment, a strip 18 of thin magnetic material is positioned along the periphery of face shield 12 and side shield 14. Alternatively, a series of small magnets could be positioned along this periphery. An additional strip 20 of magnetic material, or a series of smaller magnets, can be positioned along fastening strap 16 or along the temples or similar device used to secure safety glasses 10 to the wearer.

Safety glasses 10 are particularly suitable for use in an environment where there is a danger of flying debris, such as metal shavings, that may strike the face and endanger the eyes. The invention is particularly useful for anyone working in a workshop, auto body shop, brake shop, machine shop or similar location having a metal grinding apparatus which may generate flying metal shavings or debris.

Typically, safety glasses 10 or other shields and eyeglasses of this type are manufactured of polycarbonate or other hard transparent material. The magnetic strip 18 may be embedded in grooves provided around the edge of the face shield 12 and side shield 14. Alternatively, magnets or small magnetic strips can be clipped on, glued on, or otherwise attached in some manner to the frames of the safety glasses 10, or attached in any other way commonly known in the art. Additionally, the magnetic strips may be rounded such that they form the frames or outer edges of the polycarbonate area.

When worn, the magnetic strips 18 and 20 will tend to attract any flying metal debris which may strike the safety glasses 10 near the edges thereof, thereby preventing metal particles from infringing the facial area, and, in particular, the area surrounding the eyes. The same effect would occur with use of magnets strategically located along the periphery of the safety glasses 10.

Whereas particular embodiments of this invention have been described for purposes of illustration, it will be evident to those persons skilled in the art that numerous variations of the details of the present teaching may be made without departing from the invention as defined in the appended claims.

I claim:

1. In a pair of safety glasses having a frame for supporting a transparent eye shield and a groove provided on the periphery of the frame, the improvement comprising at least one magnetic member sized and shaped to be disposed in the groove along at least a portion of an outer surface of the frame.

2. The safety glasses of claim 1 wherein the at least one magnetic member comprises at least a portion of the frame.

3. The safety glasses of claim 1 further comprising a device for securing the safety glasses to a wearer.

4. The safety glasses of claim 3 wherein at least one magnetic member is provided along at least a portion of the securing device.

5. The safety glasses of claim 4 wherein the securing device comprises a pair of temples secured to the frame for placement along the side of the head of the wearer above the ears of the wearer.

6. The safety glasses of claim 4 wherein the securing device comprises a fastening strap secured at either end to opposing sides of the frame and adapted to be worn around the back of the head of the wearer.

7. Protective eyewear comprising a transparent face shield for covering the eyes of a wearer and a device for securing the eyewear to the wearer wherein a groove is provided on the periphery of the face shield and at least one magnet is sized and shaped to be provided along the groove in the periphery of the face shield.

8. The eyewear of claim 7 wherein the at least one magnetic member comprises at least a portion of a frame of the face shield.

9. The eyewear of claim 7 further comprising a device for securing the safety glasses to a wearer.

10. The eyewear of claim 9 wherein at least one magnetic member is provided along at least a portion of the securing device.

11. The eyewear of claim 10 wherein the securing device comprises a pair of temples secured to the face shield for placement along the side of the head of the wearer above the ears of the wearer.

12. The eyewear of claim 10 wherein the securing device comprises a fastening strap secured at either end to opposing sides of the face shield and adapted to be worn around the back of the head of the wearer.

* * * * *